(12) United States Patent
Pricop

(10) Patent No.: US 7,022,476 B2
(45) Date of Patent: Apr. 4, 2006

(54) HUMAN FCγRIIB GENE POLYMORPHISMS FOR ASSESSING DEVELOPMENT OF SYSTEMIC LUPUS ERYTHEMATOSUS AND COMPOSITIONS FOR USE THEREOF

(75) Inventor: Luminita Pricop, New York, NY (US)

(73) Assignee: New York Society for Ruptured and Crippled Maintaining the Hospital for Special Surgery, New York, NY (US)

( * ) Notice: Subject to any disclaimer, the term of this patent is extended or adjusted under 35 U.S.C. 154(b) by 198 days.

(21) Appl. No.: 10/085,484

(22) Filed: Feb. 26, 2002

(65) Prior Publication Data

US 2003/0162180 A1    Aug. 28, 2003

(51) Int. Cl.
*C12Q 1/68* (2006.01)
*G06F 19/00* (2006.01)
*C07H 21/00* (2006.01)

(52) U.S. Cl. ............................. 435/6; 702/20; 536/23.1
(58) Field of Classification Search ................. 435/7.1, 435/6; 702/22
See application file for complete search history.

(56) References Cited

U.S. PATENT DOCUMENTS 5,830,652 A    11/1998 Kimberly et al.

6,303,750 B1    10/2001 Friedman et al.
2001/0014460 A1    8/2001 Kimberly et al.

OTHER PUBLICATIONS

Mageed, RA, et al., "Immunopathology and the Gene Therapy of Lupus," Gene Therapy, 2003, vol. 10, pp. 861-874.
Takai, T., "Roles of FcReceptors in Autoimmunity," Aug. 2002, vol. 2, pp. 580-592.
Jaing, Y., et al., "Genetically Determined Aberrant Down-Regulation of FcγRIIB1 in Germinal Center B Cells Associated With Hyper-IgG and IgG Autoantibodies in Murine Systemic Lupus Erythematosus," International Immunology, Jun. 1999, vol. 11, No. 10, pp. 1685-1691.
Kyogoku, C., et al., "Fcγ Receptor Gene Polymorphisms in Japanese Patients With Systemic Lupus Erythematosus," Arthritis & Rheumatsm, May 2002, vol. 46, No. 5, pp. 1242-1254.

*Primary Examiner*—Ardin H. Marschel
*Assistant Examiner*—Pablo Whaley
(74) *Attorney, Agent, or Firm*—Darby & Darby

(57) ABSTRACT

The present invention provides methods for predicting the likelihood of development of systemic lupus erythematosus (SLE) in an individual, which comprise determining the sequence at one or more polymorphic positions within the human genes encoding FcγRIIB. The invention also provides isolated nucleic acids encoding FcγRIIB polymorphisms, nucleic acid probes that hybridize to polymorphic positions and kits for the prediction of SLE status.

7 Claims, 1 Drawing Sheet

FIGURE 1

GCCATCCTGA CATACCTCCT TGTCCTTGTT CCACAACTCA GCAGTGAGTC TGGGTTATGA

CAATAGAGAA AATTAAATGG ATGGTAGGTG GCCTGGAGTC CCCATGCTCA ATTTCAAGAA

GCATCCAGAT TCCAGGGCCT GGGTCTCCAA ATGGAAGTAG AAGTACTAGA AGATTGCTGG

TGCACGCTGT CCT G\*CATCAC CCTTTCTCAG GAGGATAGAG ACTGAAACAG GAGGTTCTGA
              C

GCTGAGTTTT GGTGACCATT TCCCTCTTTC TCCCAGAGGC CCAGGCCAGC TGTGGCCTCA

GAGGAAGAAG AAGGGAGTTG TTTCCCTAGT TTCTAAAATT TCTGTGAATT TGAACATGGG

CTACACCAGA TTTATTCTGG GAAGCTCTGA ATCTTCTAGG AGGGAAAGAC TGAGAGGAAA

GAGGGTGGAA AGGGAGGAGC CTGTGATAAA ACAGAACAT\*T TCTTTTTCAC TTCCCCTTTC
                                          A

AGACTCCAGA ATTTGTTTGC CCTCTAGGGT AGAATCGCCA AGCTTGAG A GAAGGCTGTG

ACTGCTGTGC TCTGGGCGCC ACGTCGCTCC AGGGAGTGAT GGGAATCCTG TCATTCTTAC

CTGTCCTTGC CACTGAGAGT GACTGGGCTG ACTGCAAGTC CCCCCAGCCT TGGGGTCATA

TGCTTCTGTG GACAGCTGTG CTATTCCTGG GTGAGT

SEQUENCE LISTING

<160> NUMBER OF SEQ ID NOS: 21

<210> SEQ ID NO 1
<211> LENGTH: 696
<212> TYPE: DNA
<213> ORGANISM: Artificial Sequence
<220> FEATURE:
<223> OTHER INFORMATION: Description of Artificial Sequence: human
      FcgammaRIIB

<400> SEQUENCE: 1

```
gccatcctga catacctcct tgtccttgtt ccacaactca gcagtgagtc tgggttatga      60
caatagagaa aattaaatgg atggtaggtg gcctggagtc cccatgctca atttcaagaa     120
gcatccagat tccagggcct gggtctccaa atggaagtag aagtactaga agattgctgg     180
tgcacgctgt cctgcatcac cctttctcag gaggatagag actgaaacag gaggttctga     240
gctgagtttt ggtgaccatt tccctctttc tcccagaggc ccaggccagc tgtggcctca     300
gaggaagaag aagggagttg tttccctagt ttctaaaatt tctgtgaatt tgaacatggg     360
ctacaccaga tttattctgg gaagctctga atcttctagg agggaaagac tgagaggaaa     420
gagggtggaa agggaggagc ctgtgataaa acagaacatt tctttttcac ttcccctttc     480
agactccaga atttgtttgc cctctagggt agaatcgcca agctttgaga gaaggctgtg     540
actgctgtgc tctgggcgcc acgtcgctcc agggagtgat gggaatcctg tcattcttac     600
ctgtccttgc cactgagagt gactgggctg actgcaagtc cccccagcct tggggtcata     660
tgcttctgtg gacagctgtg ctattcctgg gtgagt                               696
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 2

```
acatacctcc ttgtccttgt t                                                21
```

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 3

```
cagcccagtc actctcagt                                                   19
```

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 4

```
tgtaaaacgg ccagtacata cctccttgtc cttgtt                                36
```

<210> SEQ ID NO 5
<211> LENGTH: 24
<212> TYPE: DNA

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 5
gcagtcagcc cagtcactct cagt                                    24

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 6
tgtaaaacgg ccagtcagcc cagtcactct cagt                         34

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 7
tgacatacct ccttgtcctt gtt                                     23

<210> SEQ ID NO 8
<211> LENGTH: 9
<212> TYPE: DNA
<213> ORGANISM: Artificial Sequence
<220> FEATURE:
<223> OTHER INFORMATION: Description of Artificial Sequence:
      FcgammaRIIB promoter
<220> FEATURE:
<221> NAME/KEY: unsure
<222> LOCATION: (4)..(5)

<400> SEQUENCE: 8 ttcnnggaa                                                      9

<210> SEQ ID NO 9
<211> LENGTH: 9
<212> TYPE: DNA
<213> ORGANISM: Artificial Sequence
<220> FEATURE:
<223> OTHER INFORMATION: Description of Artificial Sequence:
      FcgammaRIIB regulatory element
<220> FEATURE:
<221> NAME/KEY: unsure
<222> LOCATION: (4)..(6)

<400> SEQUENCE: 9 ttcnnngaa                                                      9

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 10
gcgcggtacc gccatcctga catacctcct t                            31

<210> SEQ ID NO 11
<211> LENGTH: 31

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 11
gcgcctcgag cactccctgg agcgacgtgg c                                 31

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 12
ggtgcacgct gtcctccatc accctttctc a                                 31

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 13
tgagaaaggg tgatggagga cagcgtgcac c                                 31

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 14
gataaaacag aacatatctt tttcacttcc c                                 31

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 15
gggaagtgaa aaagatatgt tctgttttat c                                 31

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 16
gcagggaaat aagagagacc                                              20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 17

```
ctcagccata actttgtcag c                                              21

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 18
gggatgattg tggctgtg                                                  18

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 19
attagtggga ttggctgaa                                                 19

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 20
gactacggat acccaaatgt c                                              21

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 21
aagccagcag cagcaaaa                                                  18
```

US 7,022,476 B2

HUMAN FCγRIIB GENE POLYMORPHISMS FOR ASSESSING DEVELOPMENT OF SYSTEMIC LUPUS ERYTHEMATOSUS AND COMPOSITIONS FOR USE THEREOF

The research described herein was funded in part by the following grants: National Institute of Health, NIAMS, RO3 AR47106-01.

FIELD OF THE INVENTION

The present invention relates to genetic polymorphisms and polymorphism patterns useful for assessing development of systemic lupus erythematosus in humans. More particularly, the invention relates to identifying and using polymorphism patterns comprising a polymorphism in the human FcγIIB receptor to predict a treatment outcome or likelihood of developing systemic lupus erythematosus, and to assist in diagnosis and in prescription of an effective therapeutic regimen.

BACKGROUND OF THE INVENTION

Systemic Lupus Erythematosus

Systemic lupus erythematosus (SLE) is a chronic inflammatory disease that can affect various parts of the body including skin, blood, kidney, and joint. SLE may be a mild disease, however, may also be serious and life-threatening. More than 16,000 cases of SLE are reported in the United States each year, with up to 1.5 million cases diagnosed. Although SLE can occur at any age, and in either sex, it has been found to occur 1–15 times more frequently in women.

SLE is a prototypic immune complex disease with defects in both the humoral and efferent pathways of the immune response. Autoreactive lymphocytes initiate the process of autoantibody production and ultimately lead to formation of immune complexes. Binding of immune complexes to specific cellular receptors, called Fc receptors, can potentially modify the development or progression of SLE by altering the response of either B cell or mononuclear phagocytes to immune complex-mediated inflammation.

Immune complexes may be deposited throughout the body including in the glomeruli, skin, lungs, synovium and mesothelium. Renal disease is a common consequence of SLE. Physical manifestations of SLE include skin rashes, typically across the cheek or jaw regions, effusion in body cavities, including pericardial effusions, pericarditis, endocarditis, arthralgia and renal failure. However, there may be stages of the disease when few symptoms are evident, and patients with SLE may not necessarily exhibit identical symptoms. Some symptoms mimic other illnesses. Therefore, lupus is difficult to diagnose. To date there is no single laboratory test that can definitively detect lupus. The lupus etrythematosus cell test is not specific for SLE. The immunofluorescent antinuclear antibody (ANA) test is more specific for SLE, however, positive results are inconclusive because they may be indicative of other diseases. Skin and kidney biopsies may also be performed in an attempt to diagnose SLE.

FcγIIB Receptor

The FcγIIB receptor (FcγRIIB) is a key regulator of antibody-mediated (type II) and immune complex-mediated (type III) hypersensitivity reactions. Human low affinity Fcγ receptors IIA, IIB, IIC, IIIA and IIIB are a family of cell surface receptors, which bind IgG immune complexes (1). A different gene clustered on the long arm of chromosome 1 (1q23) encodes each FcγRII isoform, with the exception of the FcγRIIC gene, which is located telomeric on the short arm of chromosome 1 (1p36). Comparing published results of linkage studies of candidate chromosomal regions, three regions on chromosome 1 (1p13, 1q23–24, and 1q41–44) have at least two independent cohorts showing maximum log scores (the log-likelihood of the odds ratio for linkage) greater than 1 (2–5). 1q23 has been shown to be one of the strongest candidate regions for human SLE by genome-wide linkage studies (6).

Genetic variants of FcγRIIA, IIIA and IIIB and their association with SLE have been studied (7–13). The results of various association studies are inconsistent in different populations with different genetic backgrounds, raising the possibility that other gene(s) in this chromosomal region, in linkage disequilibrium with FcγRIIA, III and IIIB, may be primarily associated with SLE (14–16). Meta-analysis of studies seeking to establish a relationship between SLE and FcgR variants clearly shows that FcγRIIa-R131 is associated with SLE in African Americans, and that FcγRIIIa-F176 is associated with SLE in Caucasians and in other groups (17). Because of population admixture and small sample sizes, lack of internal control, differences in disease phenotype and the confounding influence of other inherited susceptibility factors many of the genes implicated over the years in SLE have not been confirmed and remain controversial (18).

FcγRIIB is unique in its ability to transmit inhibitory signals through an immunoreceptor tyrosine-based inhibitory motif (ITIM) in its cytoplasmic domain (19, 20).

Animal studies demonstrated a role for FcγRIIB deficiency in the development of SLE and other autoimmune disorders (21–24). Recent descriptions of deletions in the promoter region and introns of FcγRIIB in all major autoimmune prone mice strains have underscored the importance of polymorphisms in regulatory regions of FcγRIIB in influencing the expression and function of this receptor and its role in autoimmunity (25, 26). The autoimmune FcγRIIB promoter haplotype contained multiple mutations in the promoter affecting AP4 and Sp1 sites and other motifs potentially involved in transcriptional regulation. This haplotype was associated with reduced cell-surface expression of FcγRII on macrophages and activated B cells and with hyperactive macrophages and increased serum levels of IgG1 and IgG2b but not IgG2a, and is therefore likely to play an important role in the pathogenesis of SLE and other autoimmune disorders (25, 26). Three types of polymorphisms in FcγRIIB transcription regulatory regions in different mouse strains have been found (27). Autoimmune disease-prone mouse strains share two deletion sites in the promoter region and one in the third intron of FcγRIIB. Strains that are not per se autoimmune-prone, but have the potential to accelerate autoimmune diseases, share two deletion sites in the third intron (27).

As yet, there have been no reports of deficiency of inhibitory FcγRIIB function in immune complex-mediated human disease. However, polymorphisms of the human FcγRIIB gene in humans have been described. C. Kyogoku et al. (28) describe a single nucleotide polymorphisms 695T>C, representing two alleles coding for Ile (232I) and Thr (232T) within the transmembrane domain of human FcγRIIB. In an association study using 193 Japanese patients with SLE and 303 healthy individuals, the 232 T/T genotype was significantly increased in patients (10.9%) compared with healthy individuals (5.3%, ÷2=5.6, p=0.018). FcγRIIIA-176F/F showed significant association (÷2=5.8, p=0.016). Two-locus analyses revealed that, while both 3A and 2B primarily contribute to the susceptibility, previously reported association of 3B was considered to be secondary, that derived from strong linkage disequilibrium with 2B. The authors report that the frequency of this polymorphism in healthy Dutch individuals (n=148) was very low (0.7%). These results indicate that the contribution of FcγR genes to the genetic susceptibility of SLE is complex, as multiple genes within the FcγR region contribute to SLE susceptibility primarily, or in linkage disequilibrium with other FcγR genes.

K. Su (29) et al describes a haplotype (C-A) which is rare compared to the common G-T haplotype present in the first 500 bp of the FcγRIIB promoter. In an association study using 160 disease-free donors and 122 SLE patients, the authors found that these rare alleles are differentially distributed between SLE patients and non-SLE controls in African Americans (p=0.018) but not in Caucasians (p=0.088). The authors report that this rare SNP haplotype may increase expression of FcγRIIB in African American SLE patients with a resultant decrease in phagocytosis of immune complexes by monocytes/macrophages, one of the hallmarks of SLE.

Need for Effective Systemic Lupus Erythematosus Status Assessment

The problems associated with diagnosing SLE demonstrate a need in the art for methods and compositions that allow for the accurate and non-invasive determination and/or prediction of the occurrence of SLE. There is a need to reduce or eliminate trial and error in diagnosing SLE in a particular individual.

There is also a need in the art for methods and compositions that allow the identification of individuals having a predisposition to SLE, such as, e.g., sex, family history, exposure to certain environmental factors such as infection ultraviolet light, extreme stress, certain drugs such as antibiotics (sulfa, penicillin) and hormones, to facilitate early intervention and disease prevention.

The present invention addresses these and other needs in the art by providing polymorphisms and polymorphic patterns that are characteristic of systemic lupus erythematosus status, and by using these polymorphisms and patterns to assist in diagnosis or to prescribe appropriate treatments.

SUMMARY OF THE INVENTION

The invention provides methods for assessing whether a particular individual has a genetic predisposition to systemic lupus erythematosus (SLE). This aspect of the invention comprises comparing a test polymorphic pattern established by a polymorphic position within a gene encoding the FcγIIB receptor (FcγRIIB) with a polymorphic pattern of individuals having SLE. The assessment depends on whether the individual's polymorphism pattern matches the reference pattern.

The foregoing application within the scope of the invention can be deemed to be an assessment of the development of SLE in an individual, as the term is broadly defined below.

The method of the invention is carried out by comparing a test polymorphic pattern established by a polymorphic position within a gene encoding the FcγRIIB with a polymorphic pattern of a population of individuals having SLE (reference pattern). If the test pattern matches the reference pattern, there is a statistically significant probability that the individual has or may develop SLE.

In another aspect of the invention, the polymorphic pattern consists of at least two polymorphic positions in a gene encoding the FcγRIIB in an individual.

The invention also provides an isolated nucleic acid having a sequence corresponding to part or all of the gene encoding the FcγRIIB, the nucleic acid comprising a polymorphism in the FcγRIIB gene. In a preferred embodiment, the polymorphism indicates a predisposition to one or more clinical syndromes associated with SLE.

The isolated polymorphisms according to the invention include, without limitation, nucleic acids encoding FcγRIIB having one or more polymorphic positions at the position in the regulatory region numbered –385 and –119, both positions as numbered in Genbank entry X52888, numbered from the start of the first exon in the FcγRIIB promoter region.

The invention also encompasses libraries of isolated nucleic acid sequences, such as arrays on a solid surface, wherein each sequence in the library comprises a polymorphic position in the gene encoding FcγRIIB, including, without limitation, the polymorphic positions and sequences disclosed herein. Also provided are nucleic acid probes that hybridize specifically to the identified polymorphic positions; peptides and polypeptides comprising polymorphic positions; and polymorphism-specific antibodies, i.e., sequence-specific antibodies that bind differentially to polymorphic variants of FcγRIIB, that can be used to identify particular polymorphic variants.

In another aspect, the invention provides kits for the determination of polymorphic patterns in an individual's genes. The kits comprise a means for detecting polymorphic sequences, including without limitation oligonucleotide probes that hybridize at or adjacent to the polymorphic positions and polymorphism-specific antibodies.

BRIEF DESCRIPTION OF THE DRAWING

FIG. 1 shows the nucleotide sequence of the 5' promoter region of human FcγRIIB gene (SEQ ID NO:1).

DETAILED DESCRIPTION OF THE INVENTION

The invention in based, in part, on the discovery that one or more polymorphisms in certain genes in immune-complex-mediated inflammation pathways define a polymorphism pattern that correlates with the development of systemic lupus erythematosus (SLE). Most significantly, by comparing a test individual's polymorphism pattern with a reference polymorphism pattern, which is a polymorphism pattern from a population of individuals with known SLE status, one is able to predict whether the test individual has an increased likelihood to develop the same SLE status as that correlated with the reference polymorphism pattern.

The invention provides a powerful predictive tool for diagnosis and treatment of SLE. For diagnosis, the present invention permits more accurate assessment of whether an individual is suffering from SLE or is likely to develop SLE.

The present invention provides a method of distinguishing in an individual who exhibits symptoms characteristic of SLE and other diseases whether the individual has SLE or another disease. For example, it may be possible to distinguish between SLE and a disease for which a genetic disposition is not known, e.g., rheumatoid arthritis.

By evaluating a test individual's polymorphism pattern, a physician can prescribe a prophylactic or therapeutic regimen customized to that individual's SLE status or symptoms. Adverse responses to particular therapies can be avoided by excluding those individuals whose SLE status puts them at risk for that therapy. Appropriate changes in lifestyle, including diet, environmental stress, drug administration and exercise levels can be prescribed for individuals whose test polymorphic pattern matches a reference pattern that correlates with increased predisposition to SLE.

By evaluating the blood of an individual who may be suffering from SLE to determine what inflammatory factors may be present and which are correlated to differential promoter activity in an allele specific manner, a prophylactic or therapeutic regimen customized to that individual's SLE status or symptoms may be established.

In this aspect, the invention provides reagents and methods for predicting whether a particular therapeutic regime (such as a specific drug, a class of drugs, or any other therapeutic regime, pharmacological or not) would be effective in treating SLE in a human individual. The effect of agents, such as cytokines, which are present in inflammatory conditions and are involved in SLE, on specific FcγRIIB alleles and on promoter activity may be determined. Those agents identified as affecting promoter activity in an allelic specific manner may be therapeutically targeted.

In this aspect, the method of the invention is carried out by comparing a test polymorphic pattern established by a polymorphic position within a gene encoding the FcγRIIB with a polymorphic pattern of a population of individuals having SLE (reference pattern) and an identified correlation between promoter activity and polymorphic pattern. If the test pattern matches the reference pattern, the appropriate therapeutic regimen may be selected.

Definitions

"Systemic lupus erythematosus" as used herein refers to the physiological status of an individual that may have or develop systemic lupus erythematosus (SLE), as reflected in one or more markers or indicators including genotype. The methods described herein shall be deemed to include assessing the absence or presence of a pathology or symptom of SLE and the individual's predisposition to developing such a condition. Markers include, without limitation, clinical measurements, such as, e.g. skin rashes, typically across the cheek or jaw regions, effusion in body cavities, including pericardial effusions, pericarditis, endocarditis, arthralgia and renal failure. Markers according to the invention are assessed using conventional methods well known in the art. Also included in the evaluation of SLE status are quantitative or qualitative changes in markers with time, such as would be used, e.g., in the determination of an individual's response to a particular therapeutic regimen or of a predisposed individual's eventual development of SLE.

It will be understood that a diagnosis of SLE made by a medical practitioner encompasses not only clinical measurements but also medical judgment.

A "predisposition to develop systemic lupus erythematosus" refers to an increased likelihood, relative to the general population, to develop SLE, as defined above. A predisposition does not signify certainty, and development of the disease may be forestalled or prevented by prophylaxis, e.g., adopting a modified diet, exercise program, or treatment with gene therapy or pharmaceuticals. Naturally, an advantage of the present invention is that it permits identification of individuals, based on their genotype, who are predisposed to develop SLE, and for whom prophylactic intervention can be especially important.

A "polymorphism" as used herein denotes a variation in the nucleotide sequence of a gene in an individual. Genes that have different nucleotide sequences as a result of a polymorphism are "alleles." A "polymorphic position" is a predetermined nucleotide position within the sequence. In some cases, genetic polymorphisms are reflected by an amino acid sequence variation, and thus a polymorphic position can result in location of a polymorphism in the amino acid sequence at a predetermined position in the sequence of a polypeptide. An individual "homozygous" for a particular polymorphism is one in which both copies of the gene contain the same sequence at the polymorphic position. An individual "heterozygous" for a particular polymorphism is one in which the two copies of the gene contain different sequences at the polymorphic position.

A "polymorphism pattern" as used herein denotes a set of one or more polymorphisms, including without limitation single nucleotide polymorphisms, which may be contained in the sequence of a single gene or a plurality of genes. In the simplest case, a polymorphism pattern can consist of a single nucleotide polymorphism in only one position of one of two alleles of an individual. However, one has to look at both copies of a gene. A "test polymorphism pattern" as used herein is a polymorphism pattern determined for a human subject of undefined SLE status. A "reference polymorphism pattern" as used herein is determined from a statistically significant correlation of patterns in a population of individuals having SLE.

"Nucleic acid" or "polynucleotide" as used herein refers to purine- and pyrimidine-containing polymers of any length, either polyribonucleotides or polydeoxyribonucleotides or mixed polyribo-polydeoxyribo nucleotides. Nucleic acids include without limitation single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases and non-naturally occurring phosphoester analog bonds, such as phosphorothioates and thioesters. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

As used herein, the term "oligonucleotide" refers to a nucleic acid, generally of at least 10, preferably at least 15, and more preferably at least 20 nucleotides, that is hybridizable to a genomic DNA molecule, a cDNA molecule, or an mRNA molecule encoding a gene, cDNA, mRNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of a gene of interest, or to detect the presence of nucleic acids encoding the gene of interest. In a further embodiment, an oligonucleotide of the invention can form a triple helix with a double stranded sequence of interest in a DNA molecule. In still another embodiment, a library of oligonucleotides arranged on a solid support, such as a silicon wafer or chip, can be used to detect various polymorphisms of interest. Generally, oligonucleotides are prepared synthetically, preferably on a nucleic acid synthesizer. Accordingly, oligonucleotides can be prepared with non-naturally occurring phosphoester analog bonds, such as thioester bonds.

An "isolated" nucleic acid or polypeptide as used herein refers to a nucleic acid or polypeptide that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

A nucleic acid or polypeptide sequence that is "derived from" a designated sequence refers to a sequence that corresponds to a region of the designated sequence. For nucleic acid sequences, this encompasses sequences that are identical to or complementary to the sequence.

A "probe" refers to a nucleic acid or oligonucleotide that forms a hybrid structure with a sequence in a target nucleic acid due to complementarity of at least one sequence in the probe with a sequence in the target nucleic acid. Generally, a probe is labeled so it can be detected after hybridization.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989, *Molecular Cloning: A Laboratory Manual*, Second Edition, Cold Spring Harbor Laboratory Press: Cold Spring Harbor, N.Y.). The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

A "gene" for a particular protein as used herein refers to a contiguous nucleic acid sequence corresponding to a sequence present in a genome which comprises (i) a "coding region," which comprises exons (i.e., sequences encoding a polypeptide sequence or "protein-coding sequences"), introns, and sequences at the junction between exons and introns; and (ii) regulatory sequences, which flank the coding region at both 5' and 3' termini. For example, the "FcγRIIB gene" as used herein encompasses the regulatory and coding regions of the human gene encoding FcγRIIB. Typically, regulatory sequences according to the invention are located 5' (i.e., upstream) of the coding region segment. The reference sequence, obtained from Genbank, accession number X52888, was used in practicing the present invention.

The present inventor has surprisingly and unexpectedly discovered the existence of one or more genetic polymorphisms within the human gene encoding FcγRIIB which can be used to assess SLE status. In accordance with the invention, the polymorphic pattern of FcγRIIB in an individual can predict the predisposition to SLE. The invention provides methods for assessing SLE status by detecting polymorphic patterns in an individual. The present inventor has also discovered that the different allelic variants disclosed herein may be correlated to differential promoter activity and to various inflammatory factors present in an individual with SLE. In accordance with the invention, the polymorphic pattern of FcγRIIB in an individual can predict the effectiveness of a therapeutic regiment for SLE by detecting polymorphic patterns in an individual. The present invention also provides isolated nucleic acids derived from the FcγRIIB gene which comprise these polymorphisms, including probes which hybridize specifically to polymorphic positions and primers that amplify the region of the gene in which the polymorphism is located; and isolated polypeptides and peptides comprising polymorphic residues.

Methods for Assessing Systemic Lupus Erythematosus Status

The present invention provides diagnostic methods for assessing SLE status in a human individual. The methods are carried out by comparing a polymorphic position or pattern ("test polymorphic pattern") within the individual's gene encoding FcγRIIB with the polymorphic patterns of humans having SLE ("reference polymorphic pattern").

For any meaningful prediction, the polymorphic pattern of the individual is identical to the polymorphic pattern of individuals who exhibit SLE status markers or symptoms.

In another embodiment, the method involves comparing an individual's polymorphic pattern with polymorphic patterns of individuals who exhibit or have exhibited one or more markers of SLE, such as, e.g., skin rashes, typically across the cheek or jaw regions, effusion in body cavities, including pericardial effusions, pericarditis, endocarditis, arthralgia and renal failure, and drawing analogous conclusions as to the individual's predisposition to developing SLE, as detailed above.

Identification of Polymorphic Patterns

In practicing the methods of the invention, an individual's polymorphic pattern can be established, e.g., by obtaining DNA from the individual and determining the sequence at a predetermined polymorphic position or positions in a gene, or more than one gene.

The DNA may be obtained from any cell source. Non-limiting examples of cell sources available in clinical practice include, without limitation, blood cells, buccal cells, cervicovaginal cells, epithelial cells from urine, fetal cells, or any cells present in tissue obtained by biopsy. Cells may also be obtained from body fluids, including, without limitation, blood, saliva, sweat, urine, cerebrospinal fluid, feces, and tissue exudates at the site of infection or inflammation. DNA is extracted from the cell source or body fluid using any of the numerous methods that are standard in the art. It will be understood that the particular method used to extract DNA will depend on the nature of the source.

Determination of the sequence of the extracted DNA at polymorphic positions is achieved by any means known in the art, including but not limited to direct sequencing, hybridization with allele-specific oligonucleotides, allele-specific PCR, ligase-PCR, HOT cleavage, denaturing gradient gel electrophoresis (DGGE), and single-stranded conformational polymorphism (SSCP). Direct sequencing may be accomplished by any method, including without limitation chemical sequencing, using the Maxam-Gilbert method; by enzymatic sequencing, using the Sanger method; mass spectrometry sequencing; and sequencing using a chip-based technology. See, e.g., Little et al., *Genet. Anal.* 6:151, 1996. Preferably, DNA from a subject is first subjected to amplification by polymerase chain reaction (PCR) using specific amplification primers.

In an alternate embodiment, biopsy tissue is obtained from a subject. Antibodies that are capable of distinguishing between different isoforms of FcγRIIB are then applied to samples of the tissue to determine the presence or absence of a polymorphic form specified by the antibody. The antibodies may be polyclonal or monoclonal, preferably monoclonal. Measurement of specific antibody binding to cells may be accomplished by any known method, e.g., quantitative flow cytometry, or enzyme-linked or fluorescence-linked immunoassay. The presence or absence of a particular polymorphism or polymorphic pattern, and its allelic distribution (i.e., homozygosity vs. heterozygosity) is determined by comparing the values obtained from a patient with norms established from populations of patients having known polymorphic patterns.

In another alternate embodiment, RNA is isolated from biopsy tissue using standard methods well known to those of ordinary skill in the art such as guanidium thiocyanate-phenol-chloroform extraction (Chomocyznski et al., 1987, *Anal. Biochem.*, 162:156.) The isolated RNA is then subjected to coupled reverse transcription and amplification by polymerase chain reaction (RT-PCR), using specific oligonucleotide primers that are specific for a selected polymorphism. Conditions for primer annealing are chosen to ensure specific reverse transcription and amplification; thus, the appearance of an amplification product is diagnostic of the presence of a particular polymorphism. In another embodiment, RNA is reverse-transcribed and amplified, after which the amplified sequences are identified by, e.g., direct sequencing. In still another embodiment, cDNA obtained from the RNA can be cloned and sequenced to identify a polymorphism.

Establishing Reference Polymorphism Patterns

In practicing the present invention, the distribution of polymorphic patterns in a large number of individuals exhibiting SLE status is determined by any of the methods described above, and compared with the distribution of polymorphic patterns in patients that have been matched for age, ethnic origin, and/or any other statistically or medically relevant parameters, who exhibit quantitatively or qualitatively different systemic lupus erythematosus status. Correlations are achieved using any method known in the art, including nominal logistic regression or standard least squares regression analysis. In this manner, it is possible to establish statistically significant correlations between particular polymorphic patterns and SLE status.

A statistically significant correlation preferably has a "p" value of less than or equal to 0.05. Any standard statistical method can be used to calculate these values, such as the normal Student's T Test, or Fischer's Exact Test.

The identity and number of polymorphisms to be included in a reference pattern depends not only on the prevalence of a polymorphism and its predictive value for the particular use, but also on the value of the use and its requirement for accuracy of prediction. The greater the predictive value of a polymorphism, the lower the need for inclusion of more than one polymorphism in the reference pattern. However, if a polymorphism is very rare, then its absence from an individual's pattern might provide no indication as to whether the individual has a particular status. Under these circumstances, it might be advisable to select instead two or more polymorphisms which are more prevalent. Even if none of them has a high predictive value on its own, the presence of more than one of them might be sufficiently predictive for the particular purpose.

In establishing reference polymorphism patterns, it is desirable to use a defined population. For example, tissue libraries collected and maintained by state or national departments of health can provide a valuable resource, since genotypes determined from these samples can be matched with medical history, and particularly SLE status, of the individual. As can be readily understood by one of ordinary skill in the art, specific polymorphisms may be associated with a closely linked population. However, other polymorphisms in the same gene may correlate with SLE status of other genetically related populations. Thus, in addition to the specific polymorphisms provided in the instant application, the invention identifies genes in which any polymorphisms can be used to establish reference and test polymorphism patterns for evaluating SLE status of individuals in the population.

In a specific embodiment, DNA samples can be obtained from a depository of samples from a selected population based on their medical history. Such a depository is found, for example, at the Hospital for Special Surgery Autoimmune Registry and Repository.

In a specific embodiment, DNA sequence analysis can be carried out by: (i) amplifying short fragments of each of the genes using polymerase chain reaction (PCR) and (ii) sequencing the amplified fragments. The sequences obtained from each individual can then be compared with known sequences, e.g., Genbank Accession No. X52888, to identify polymorphic positions.

Comparing Test Patterns to Reference Patterns

As noted above, the test pattern from an individual can be compared to a reference pattern established for a predetermined SLE status. Identity between the test pattern and the reference pattern means that the tested individual has a probability of developing SLE. As discussed above, this probability depends on the prevalence of the polymorphism and the statistical significance of its correlation with SLE status.

Polymorphic Positions

Polymorphic positions in the genes encoding FcγRIIB which are encompassed by the invention are identified by determining the DNA sequence of all or part of the FcγRIIB gene in a multiplicity of individuals in a population. DNA sequence determination may be achieved using any conventional method, including, e.g., chemical or enzymatic sequencing.

The polymorphic positions of the gene for use in the invention include without limitation FcγRIIB positions in the regulatory region numbered −385 and −119 as numbered from the start of the first exon in GenBank entry X52888.

In one embodiment, an individual may be homozygous at position −385 (C/C). In another embodiment, an individual may be homozygous at position −119 (A/A). In yet another embodiment, an individual may be heterozygous at position −119 (T/A).

The polymorphic patterns comprising one or more of these polymorphisms in the FcγRIIB gene according to the invention were correlated with an increased incidence of SLE.

Isolated Polymorphic Nucleic Acids Vectors, Probes & Primers and Arrays

Vectors for Expression of Polymorphic Variants of Fcgamma IIB Receptor

The present invention provides isolated nucleic acids comprising the polymorphic positions described above for the human FcγRIIB gene; vectors comprising the nucleic acids; and transformed host cells comprising the vectors. The invention also provides probes which are useful for detecting these polymorphisms.

The nucleic acids encoding a FcγRIIB comprising a polymorphism that is useful for determining SLE status of an individual is particularly valuable for screening, whether by direct screening of the nucleic acid with the polymorphism, or by screening the polypeptide expressed by that nucleic acid.

In practicing the present invention, many conventional techniques in molecular biology, microbiology, and recombinant DNA, are used. Such techniques are well known and are explained fully in, for example, Sambrook et al., 1989, *Molecular Cloning: A Laboratory Manual,* Second Edition, Cold Spring Harbor Laboratory Press, Cold Spring Harbor, N.Y.; *DNA Cloning: A Practical Approach,* Volumes I and II, 1985 (D. N. Glover ed.); *Oligonucleotide Synthesis,* 1984, (M. L. Gait ed.); *Nucleic Acid Hybridization,* 1985, (Hames and Higgins); Ausubel et al., *Current Protocols in Molecular Biology,* 1997, (John Wiley and Sons); and *Methods in Enzymology* Vol. 154 and Vol. 155 (Wu and Grossman, and Wu, eds., respectively).

Insertion of nucleic acids (typically DNAs) comprising the sequences of the present invention into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, any site desired may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., 1988, *Science* 239:48. The cleaved vector and the DNA fragments may also be modified if required by homopolymeric tailing.

The nucleic acids may be isolated directly from cells or may be chemically synthesized using known methods. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by native FcγRIIB gene sequences, or may be associated with heterologous sequences, including promoters, enhancers, response elements, signal sequences, polyadenylation sequences, introns, 5'- and 3'-noncoding regions, and the like.

The invention also provides nucleic acid vectors comprising the disclosed FcγRIIB-derived gene sequences or derivatives or fragments thereof. A large number of vectors, including plasmid and fungal vectors, have been described for replication and/or expression in a variety of eukaryotic and prokaryotic hosts, and may be used for gene therapy as well as for simple cloning or protein expression. Non-limiting examples of suitable vectors include without limitation pUC plasmids, pET plasmids (Novagen, Inc., Madison, Wis.), or pRSET or pREP (Invitrogen, San Diego, Calif.), and many appropriate host cells, using methods disclosed or cited herein or otherwise known to those skilled in the relevant art. The particular choice of vector/host is not critical to the practice of the invention.

Suitable host cells may be transformed/transfected/infected as appropriate by any suitable method including electroporation, $CaCl_2$ mediated DNA uptake, calcium phosphate precipitation, fungal or viral infection, lipofection, microinjection, microprojectile, or other established methods. Appropriate host cells included bacteria, archebacteria, fungi, especially yeast, and plant and animal cells, especially mammalian cells. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced FcγRIIB-derived peptides and polypeptides.

Nucleic acids encoding FcγRIIB-derived gene sequences may also be introduced into cells by recombination events. For example, such a sequence can be introduced into a cell and thereby effect homologous recombination at the site of an endogenous gene or a sequence with substantial identity to the gene. Other recombination-based methods such as nonhomologous recombinations or deletion of endogenous genes by homologous recombination may also be used.

Oligonucleotides

The nucleic acids of the present invention find use as probes for the detection of genetic polymorphisms, as primers for the expression of polymorphisms, or in molecular library arrays for high throughput screening.

Probes in accordance with the present invention comprise without limitation isolated nucleic acids of about 10–100 bp, preferably 15–75 bp and most preferably 17–25 bp in length, which hybridize at high stringency to one or more of the FcγRIIB gene-derived polymorphic sequences disclosed herein or to a sequence immediately adjacent to a polymorphic position. Furthermore, in some embodiments a full-length gene sequence may be used as a probe. In one series of embodiments, the probes span the polymorphic positions in the genes disclosed above. In another series of embodiments, the probes correspond to sequences immediately adjacent to the polymorphic positions.

The oligonucleotide nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. PNAs are also included. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

PCR amplification of FcγRIIB gene segments that contain a polymorphism provides a powerful tool for detecting the polymorphism. The oligonucleotides of the invention can also be used as PCR primers to amplify segments of FcγRIIB containing a polymorphism of interest. The amplified segment can be evaluated for the presence or absence of a polymorphism by restriction endonuclease activity, SSCP, or by direct sequencing. In another embodiment, the primer is specific for a polymorphic sequence on the gene. If the polymorphism is present, the primer can hybridize and DNA will be produced by PCR. However, if the polymorphism is absent, the primer will not hybridize, and no DNA will be produced. Thus, PCR can be used to directly evaluate whether a polymorphism is present or absent.

Molecular library arrays of oligonucleotides (including oligonucleotides with modifications as described above) are another powerful tool for rapidly assessing whether one or more polymorphisms are present in a FcγRIIB gene, preferably in combination with other genes. Molecular library arrays are disclosed in U.S. Pat. Nos. 5,677,195, 5,599,695, 5,545,531, and 5,510,270.

Polypeptides and Polymorphism-Specific Antibodies

The present invention encompasses isolated peptides and polypeptides encoded by all or a portion of FcγRIIB genes comprising polymorphic positions disclosed above. In one preferred embodiment, the peptides and polypeptides are useful screening targets to identify drugs to treat SLE. In another preferred embodiment, the peptides and polypeptides are capable of eliciting antibodies in a suitable host animal that react specifically with a polypeptide comprising the polymorphic position and distinguish it from other polypeptides having a different amino acid sequence at that position.

Polypeptides according to the invention are preferably at least five or more residues in length, preferably at least fifteen residues. Methods for obtaining these polypeptides are described below. Many conventional techniques in protein biochemistry and immunology are used. Such techniques are well known and are explained in *Immunochemical Methods in Cell and Molecular Biology*, 1987 (Mayer and Waler, eds; Academic Press, London); Scopes, 1987, *Protein Purification: Principles and Practice*, Second Edition (Springer-Verlag, N.Y.) and *Handbook of Experimental Immunology*, 1986, Volumes I–IV (Weir and Blackwell eds.).

Nucleic acids comprising protein-coding sequences can be used to direct the recombinant expression of FcγRIIB-derived polypeptides in intact cells or in cell-free translation systems. The known genetic code, tailored if desired for more efficient expression in a given host organism, can be used to synthesize oligonucleotides encoding the desired amino acid sequences. The polypeptides may be isolated from human cells, or from heterologous organisms or cells (including, but not limited to, bacteria, fungi, insect, plant, and mammalian cells) into which an appropriate protein-coding sequence has been introduced and expressed. Furthermore, the polypeptides may be part of recombinant fusion proteins.

Peptides and polypeptides may be chemically synthesized by commercially available automated procedures, including, without limitation, exclusive solid phase synthesis, partial solid phase methods, fragment condensation or classical solution synthesis. The polypeptides are preferably prepared by solid phase peptide synthesis as described by Merrifield, 1963, *J. Am. Chem. Soc.* 85:2149.

Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against FcγRIIB or against peptides derived therefrom, can be used as purification reagents. Other purification methods are possible.

The present invention also encompasses derivatives and homologues of the polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

The present invention also encompasses antibodies that specifically recognize the polymorphic positions of the invention and distinguish a peptide or polypeptide containing a particular polymorphism from one that contains a different sequence at that position. Such polymorphic position-specific antibodies according to the present invention include polyclonal and monoclonal antibodies. The antibodies may be elicited in an animal host by immunization with ATZ-derived immunogenic components or may be formed by in vitro immunization of immune cells. The immunogenic components used to elicit the antibodies may be isolated from human cells or produced in recombinant systems. The antibodies may also be produced in recombinant systems programmed with appropriate antibody-encoding DNA. Alternatively, the antibodies may be constructed by biochemical reconstitution of purified heavy and light chains. The antibodies include hybrid antibodies (i.e., containing two sets of heavy chain/light chain combinations, each of which recognizes a different antigen), chimeric antibodies (i.e., in which either the heavy chains, light chains, or both, are fusion proteins), and univalent antibodies (i.e., comprised of a heavy chain/light chain complex bound to the constant region of a second heavy chain). Also included are Fab fragments, including Fab' and F(ab)$_2$ fragments of antibodies. Methods for the production of all of the above types of antibodies and derivatives are well-known in the art and are discussed in more detail below. For example, techniques for producing and processing polyclonal antisera are disclosed in Mayer and Walker, 1987, *Immunochemical Methods in Cell and Molecular Biology*, (Academic Press, London). The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., Schreier et al., 1980, *Hybridoma Techniques;* U.S. Pat. Nos. 4,341,761; 4,399,121; 4,427,783; 4,444,887; 4,466,917; 4,472,500; 4,491,632; and 4,493,890. Panels of monoclonal antibodies produced against-derived epitopes can be screened for various properties; i.e. for isotype, epitope affinity, etc.

The antibodies of this invention can be purified by standard methods, including but not limited to preparative disc-gel electrophoresis, isoelectric focusing, HPLC, reversed-phase HPLC, gel filtration, ion exchange and partition chromatography, and countercurrent distribution. Purification methods for antibodies are disclosed, e.g., in *The Art of Antibody Purification,* 1989, Amicon Division, W. R. Grace & Co. General protein purification methods are described in *Protein Purification: Principles and Practice,* R. K. Scopes, Ed., 1987, Springer-Verlag, New York, N.Y.

Methods for determining the immunogenic capability of the disclosed sequences and the characteristics of the resulting sequence-specific antibodies and immune cells are well-known in the art. For example, antibodies elicited in response to a peptide comprising a particular polymorphic sequence can be tested for their ability to specifically recognize that polymorphic sequence, i.e., to bind differentially to a peptide or polypeptide comprising the polymorphic sequence and thus distinguish it from a similar peptide or polypeptide containing a different sequence at the same position.

Diagnostic Methods and Kits

The present invention provides kits for the determination of the sequence at a polymorphic position or positions within the FcγRIIB gene in an individual. The kits comprise a means for determining the sequence at the polymorphic positions, and may optionally include data for analysis of polymorphic patterns. The means for sequence determination may comprise suitable nucleic acid-based and immunological reagents (see below). Preferably, the kits also comprise suitable buffers, control reagents where appropriate, and directions for determining the sequence at a polymorphic position. The kits may also comprise data for correlation of particular polymorphic patterns with desirable treatment regimens or other indicators.

Nucleic-Acid-Based Diagnostic Methods and Kits

The invention provides nucleic acid-based methods for detecting polymorphic patterns in a biological sample. The sequence at particular polymorphic positions in the genes is determined using any suitable means known in the art, including without limitation hybridization with polymorphism-specific probes and direct sequencing.

The present invention also provides kits suitable for nucleic acid-based diagnostic applications. In one embodiment, diagnostic kits include the following components:
 (i) Probe DNA: The probe DNA may be pre-labelled; alternatively, the probe DNA may be unlabelled and the ingredients for labelling may be included in the kit in separate containers; and
 (ii) Hybridization reagents: The kit may also contain other suitably packaged reagents and materials needed for the particular hybridization protocol, including solid-phase matrices, if applicable, and standards.
In another embodiment, diagnostic kits include:
 (i) Sequence determination primers: Sequencing primers may be pre-labelled or may contain an affinity purification or attachment moiety; and
 (ii) Sequence determination reagents: The kit may also contain other suitably packaged reagents and materials needed for the particular sequencing protocol. In one preferred embodiment, the kit comprises a panel of sequencing primers, whose sequences correspond to sequences adjacent to the polymorphic positions.

Antibody-Based Diagnostic Methods and Kits

Antibody-based methods for detecting polymorphic patterns in a biological sample may also be used. The methods comprise the steps of: (i) contacting a sample with one or more antibody preparations, wherein each of the antibody preparations is specific for a particular polymorphic form of the FcγRIIB under conditions in which a stable antigen-antibody complex can form between the antibody and antigenic components in the sample; and (ii) detecting any antigen-antibody complex formed in step (i) using any suitable means known in the art, wherein the detection of a complex indicates the presence of the particular polymorphic form in the sample.

Typically, immunoassays use either a labelled antibody or a labelled antigenic component (e.g., that competes with the antigen in the sample for binding to the antibody).

Suitable labels include without limitation enzyme-based, fluorescent, chemiluminescent, radioactive, or dye molecules. Assays that amplify the signals from the probe are also known, such as, for example, those that utilize biotin and avidin, and enzyme-labelled immunoassays, such as ELISA assays.

The foregoing reagents may be provided in kits suitable for antibody-based diagnostic applications. Diagnostic kits typically include one or more of the following components:

(i) Polymorphism-specific antibodies: The antibodies may be pre-labelled; alternatively, the antibody may be unlabelled and the ingredients for labelling may be included in the kit in separate containers, or a secondary, labelled antibody is provided; and (ii) Reaction components: The kit may also contain other suitably packaged reagents and materials needed for the particular immunoassay protocol, including solid-phase matrices, if applicable, and standards.

The kits referred to above may include instructions for conducting the test. Furthermore, in preferred embodiments, the diagnostic kits are adaptable to high-throughput and/or automated operation.

Drug Targets and Screening Methods

Nucleotide sequences derived from the gene encoding a polymorphic form of FcγRIIB, and peptide sequences derived from that polymorphic form of FcγRIIB, may be useful targets to identify SLE drugs, i.e., compounds that are effective in treating one or more clinical symptoms of SLE. Drug targets include without limitation (i) isolated nucleic acids derived from the gene encoding FcγRIIB and (ii) isolated peptides and polypeptides derived from FcγRIIB polypeptides, each of which comprises one or more polymorphic positions.

In Vitro Screening Methods

In one embodiment, an isolated nucleic acid comprising one or more polymorphic positions is tested in vitro for its ability to bind test compounds in a sequence-specific manner. The methods comprise:

(i) providing a first nucleic acid containing a particular sequence at a polymorphic position and a second nucleic acid whose sequence is identical to that of the first nucleic acid except for a different sequence at the same polymorphic position;

(ii) contacting the nucleic acids with a multiplicity of test compounds under conditions appropriate for binding; and (iii) identifying those compounds that bind selectively to either the first or second nucleic acid sequence.

Selective binding as used herein refers to any measurable difference in any parameter of binding, such as, e.g., binding affinity, binding capacity, etc.

In another embodiment, an isolated peptide or polypeptide comprising one or more polymorphic positions is tested in vitro for its ability to bind test compounds in a sequence-specific manner. The screening methods involve:

(i) providing a first peptide or polypeptide containing a particular sequence at a polymorphic position and a second peptide or polypeptide whose sequence is identical to the first peptide or polypeptide except for a different sequence at the same polymorphic position;

(ii) contacting the polypeptides with a multiplicity of test compounds under conditions appropriate for binding; and (iii) identifying those compounds that bind selectively to one of the nucleic acid sequences.

In preferred embodiments, high-throughput screening protocols are used to survey a large number of test compounds for their ability to bind the genes or peptides disclosed above in a sequence-specific manner.

Test compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means.

In Vivo Screening Methods

Intact cells or whole animals expressing polymorphic variants of a gene encoding FcγRIIB can be used in screening methods to identify candidate SLE drugs.

In one series of embodiments, a permanent cell line is established from an individual exhibiting a particular polymorphic pattern. Alternatively, cells (including without limitation mammalian, insect, yeast, or bacterial cells) are programmed to express a gene comprising one or more polymorphic sequences by introducing appropriate DNA. Candidate compounds can be identified using any suitable assay, including without limitation (i) assays that measure selective binding of test compounds to particular polymorphic variants of FcγRIIB (ii) assays that measure the ability of a test compound to modify (i.e., inhibit or enhance) a measurable activity or function of the FcγRIIB and (iii) assays that measure the ability of a compound to modify (i.e., inhibit or enhance) the transcriptional activity of sequences derived from the promoter (i.e., regulatory) regions the FcγRIIB gene.

In another embodiment, transgenic animals are created in which (i) a human FcγRIIB having different sequences at particular polymorphic positions are stably inserted into the genome of the transgenic animal; and/or (ii) the endogenous FcγRIIB genes are inactivated and replaced with human FcγRIIB genes having different sequences at particular polymorphic positions. See, e.g., Coffinan, *Semin. Nephrol.* 17:404, 1997; Esther et al., Lab. Invest. 74:953, 1996; Murakami et al., *Blood Press. Suppl.* 2:36, 1996. Such animals can be treated with candidate compounds and monitored for one or more clinical markers of SLE status.

The discovery of differential promoter activity in the FcγRIIB gene is useful to identify factors which, there is an inflammatory milieu, which might affect promoter activity "in vivo" and especially under disease states. The invention is useful to identify conditions, such as combinations of cytokines, which would mimic the inflammatory conditions present in SLE. Under these "inflammatory" conditions, the differential promoter activity of certain alleles might differ. Once identified, the conditions which affect promoter activity in an allele specific way can be therapeutically targeted.

The following are intended as non-limiting examples of the invention.

EXAMPLE 1

Identification of Polymorphic Positions in Human Genes Encoding FcγRIIB Associated with SLE A. Identification of Polymorphic Positions The following studies were performed to identify polymorphic residues within the genes encoding human FcγRIIB.

A 536 bp region of the 5' untranslated region (5' UTR) (SEQ ID NO: 1) of the human FcγRIIB gene in over 300 donors was sequenced.

Genotyping by polymerase chain reaction (PCR) followed by dye primer sequence analysis was performed. The FcγRIIB promoter was amplified using the following primers: forward primer 5'-ACATACCTCCTTGTCCTTGTT-3' (SEQ ID NO: 2) and reverse primer 5'-CAGCCCAGT-CACTCTCAGT-3' (SEQ ID NO: 3) to produce amplicons of about 800 bp. The primers for forward dye primer sequencing had the M13 tag linked to the 5' end of the forward primer 5'-TGT AAA ACG GCC AGT ACA TAC CTC CTT GTC CTT GTT 3' (SEQ ID NO: 4); reverse primer 5' GCA GTC AGC CCA GTC ACT CTC AGT (SEQ ID NO:5). Primers for reverse sequencing had M13 linked to the 5' end of the reverse primer 5' TGT AAA ACG GCC AGT CAG CCC AGT CAC TCT CAG T 3' (SEQ ID NO:6); forward primer 5' TGA CAT ACC TCC TTG TCC TTG TT 3' (SEQ ID NO:7). The amplification was performed for 30 cycles of 94°, 1 min; 58° C., 1 min; 72° C., 1 min. PCR products were concentrated using YM-100 microcons (Millipore). Sequencing was performed in the Molecular Biology Core Facility at the Hospital for Special Surgery using Dye Primer Sequencing Ready Reaction-21 M13 kit (Perkin Elmer/Applied Biosystems) and analyzed on an ABI Prism 377 automatic DNA sequencer. Initial sequencing data of this region showed high 100 homology with the published FcγRIIB 5' sequence in the majority of normal control subjects.

A SNP was identified containing a heterozygous G to C polymorphism at position −385 from the start of the first exon (or −343 from the transcription initiation site) in the FcγRIIB promoter of several normal individuals.

B. Identification of the Frequency of the Polymorphisms

The frequency of these alleles in the FcγRIIB promoter sequence from genomic DNA in normal controls and SLE patients was examined. Genomic DNA from PBMC of normal volunteers from Hospital for Special Surgery and obtained written consent from all subjects. Genomic DNA from Caucasian SLE patients, coded and stored in the Hospital for Special Surgery Autoimmune Registry and Repository, was used. In all cases, blood samples were obtained from blood taken during routine clinical analysis. Caucasian control DNA was obtained from blood from healthy volunteers, aged 20–65 yr by using the DNA Isolation Kit (Gentra, Minn.).

The presence of the (−385 G/C) heterozygous genotype and the −385 homozygous C/C genotype was confirmed by sequencing 164 Caucasian SLE patients and 102 Caucasian non-SLE controls. The −385C/C genotype was present in 7.9% of SLE patients vs 0.98% Caucasian non-SLE controls, and was significantly (P=0.034) higher in SLE patients than in healthy adults. Table 1 shows the distribution of alleles of the FcγRIIB promoter in SLE patients and healthy controls.

The odds ratio for −385 C/C homozygous individuals to develop SLE was 8.7 compared to those who were not −385 C/C homozygous (−385 G/C or −385 G/G), p=0.02 (two sided Fisher's exact test), 95% confidence interval on odds ratio 1.3–373. The actual number of alleles in normal individuals (182G and 22C) compared to individuals with lupus (278G and 50C) was not significantly different (p=0.183).

TABLE 1

| Genotype* (% of group) | | | | | | | |
|---|---|---|---|---|---|---|---|
| SLE patients (n = 164) | | | | Non-SLE controls (n = 102) | | | |
| G/G | 127 (77.4%) | T/T | 126 (76.8%) | G/G | 81 (79.4%) | T/T | 79 (77.5%) |
|  |  | T/A | 1 (0.6%) |  |  | T/A | 2 (1.9%) |
| G/C | 24 (14.6%) | T/T | 24 | G/C | 20 (19.6%) | T/T | 20 |
| C/C | 13 (7.9%) | A/A | 3 (1.8%) | C/C | 1 (0.98%) | A/A | 1 |
|  |  | T/A | 2 (1.2%) |  |  |  |  |
|  |  | T/T | 8 (4.9%) |  |  |  |  |

*SLE patients vs. normal controls; 3 × 2 contingency table, Chi-square = 6.737, P = 0.034
n = No. of subjects In the process of sequencing the proximal promoter region of the human FcγRIIB gene in reverse direction, a second SNP (T to A) was identified, at position −119 relative to the start of the first exon (or position −77 from the transcription initiation site). The homozygous −119 A/A genotype was identified in four donors, who were also homozygous C/C at the −385 locus, three of which had SLE. The heterozygous −119 T/A genotype was identified in 3 additional SLE donors and 2 normal controls.

The results suggest that C is associated with A in both lupus (p<0.001) and normals (p=0.02), and that C/C differs from the G carrying group in the T-A distribution.

The distribution of FcγRIIB promoter alleles was studied in different ethnic backgrounds. The −385C allele was not detected in any of the 26 DNA samples obtained from Korean SLE patients and only one out of 52 African American SLE patients was G/C heterozygous. In order to determine the frequency of the (−119 T to A) SNP, reverse sequencing of the FcγRIIB promoter in these patients is performed. The distribution of FcγRIIB promoter alleles in four ethnically matched SLE and disease free populations, Caucasian, African American, Hispanic and Asian, is compared.

The FcγRIIB promoter sequence in patients with early onset of SLE was studied by sequencing DNA obtained from the Pediatric Lupus Registry at the Hospital for Special Surgery. All sequences performed from genomic DNA from 5 Caucasian SLE pediatric patients and 16 Hispanic pediatric patients showed the common genotype −385 G/G and −119 T/T.

The sequence of the FcγRIIB promoter in genomic DNA from rheumatoid arthritis (RA) patients was analyzed. The DNA was obtained from the RA Registry at the Hospital for Special Surgery. The FcγRIIB promoter was sequenced by dye primer sequencing in 111 RA patients of which 61 were Caucasian, 6 were Hispanic, 4 were African American, 3 were Asian and 37 were of unknown ethnicity. Of the 111 RA patients studied 96 were −385 G/G homozygous and 13 were −385 G/C heterozygous. In the cohort of Caucasian RA patients studied 2 were −385 C/C homozygous, one of which was also heterozygous −119 T/A.

EXAMPLE 2

Polymorphisms and Differential Promoter Activity of human FCγRIIB

The biological activity of the FcγRIIB promoter allelic polymorphisms was studied in a reporter construct assay to determine whether the polymorphisms result in differential promoter activity.

Described regulatory elements of the FcγRIIB genes are located in the promoter region located upstream of the transcription initiation site. The regulation of gene transcription by gamma interferon (INF-g), a prototypic Th1 cytokine, is mediated by a promoter sequence 5'-TTCNNGGAA-3' (SEQ ID NO: 8) with the potential to bind STAT1. Several STAT binding sites are present in the promoter of human FcγRIIB genes. A similar 9-bp consensus sequence 5'-TTCNNNGAA-3' (SEQ ID NO:9) is a potential STAT 6 binding site, which is preferentially activated by IL-4, a TH2 cytokine. A glucocorticoid response element (GRE) required for binding of the glucocorticoid receptor DNA-binding domain is present in the promoter of FcγRIIB genes. One of the polymorphisms identified herein is contained within the GRE sequence of the FcγRIIB promoter.

PCR primers were designed to amplify a 579-bp fragment of the FcγRIIB 5'-flanking sequence. Primers containing GC clamps and recognition sites for Kpn I in the forward primer 5'-GCGC GGTACCGCCATCCTGACATACCTCCTT-3' (SEQ ID NO: 10) and Xho I in the reverse primer 5'-GCGC-CTCGAGCACTCCCTGGAGCGACGTGGC-3' (SEQ ID NO: 11) were used to produce products containing either a G or a C at the −385 position. PCR conditions: 94° C. for 1 min, 55° C. for 1 min, and 72° C. for 1 min for 25 cycles. After restriction enzyme digestion, the products were directionally ligated into the Kpn I/Xho I site of the pGL3 or pGL3-Enhancer vectors (Promega, Madison, Wis.). The resulting constructs carry the luciferase reporter gene under the control of the different FcgRIIB promoters. Constructs were verified by automated sequencing before use in experiments.

P-GL3-enhancer vector constructs containing the wild type version of the 578 bp proximal portion of the FcγRIIB promotor were mutated at two sites via site directed mutagenesis. The 5'-flanking sequence (promoter and 5'UTR) of FcγRIIB was amplified using genomic DNA from donors bearing the common −385 G/G genotype (WT) cloned in the pGL3-Enhancer vector. We replaced additional FcγRIIB promoter nucleotides at the −385 (C) locus and the −119 (A) locus, and at both loci (C+A) by site-directed mutagenesis, to match all the haplotypes that we identified by sequencing genomic DNA. Mutations were performed using the Stratagene Quick Change kit, and specific primers from Invitrogen. One pair of primers was used to change the −385 base from G to C: forward primer 5' GGT GCA CGC TGT CCT CCA TCA CCC TTT CTC A 3' (SEQ ID NO:12) and reverse primer 5' TGA GAA AGG GTG ATG GAG GAC AGC GTG CAC C 3' SEQ ID NO:13). Another primer pair was used to change the −119 base from T to A: forward primer 5' GAT AAA ACA GAA CAT ATC TTT TTC ACT TCC C 3' (SEQ ID NO:14) and reverse primer 5' GGG AAG TGA AAA AGA TAT GTT CTG TTT TAT C 3' (SEQ ID NO:15). PCR was performed on the wild type construct with each of the two primer sets according to the conditions specified by Stratagene (95° C., 30 sec, then 12 cycles of 95° C., 30 sec; 55° C., 1 min.; 68° C. 2min). Subsequently, PCR products were digested with Dpn I restriction enzyme to remove the parental (wild type) construct. PCR products were then transformed into JM-109 E. coli and plated on LB ampicillin plates. Isolated colonies were grown in LB ampicillin. The plasmids were purified and the presence of the desired mutation was confirmed by dye terminator cycle sequencing (Applied Biosystems).

To examine whether individual or combined SNPs change promoter activity, U937 (ATCC) cells were transfected with each reporter plasmid and a control plasmid encoding the renilla luciferase gene, and were analyzed in a luciferase reporter gene assay. U937 (ATCC, Rockville, Md.) cells were grown in tissue culture flasks in RPMI, supplemented with 10% heat inactivated fetal calf serum, L-glutamine, sodium bicarbonate and penicillin (50 U/ml)/streptomycin (50 ug/ml). Cells were harvested approximately one hour before transfection and washed in RPMI, then resuspended in Optimem medium (Invitrogen) at a concentration of 1.6×106 cells/ml. Cells were plated in 24 well polystyrene plates at 250 ul per well (4×105 cells per transfection). Each plasmid of interest was diluted in Optimem at a concentration of 10 ug/ml along with renilla plasmid at a final concentration of 3 ug/ml. LipofectAMINE 2000 reagent (Invitrogen) was diluted 1/20(v/v) in Optimem and an equal volume of this was added to the diluted plasmids of interest plus renilla, or renilla alone. Following a 20 minute incubation of plasmid with LipofectAMINE, 100 ul of the mixture was added to each well of cells and transfection took place during a 4 hour incubation at 37° C. Following transfection cells were harvested from the 24 well plates to polypropylene culture tubes and cultured for 24 hours either with 10% FCS medium alone, or with medium plus interferon-g (400 U/ml) or Dexamethasone ($10^{-7}$M). After 24 hours, cells were washed in PBS, then lysed in 100 ul passive lysis buffer (Promega) for 20 minutes. Lysates were centrifuged and triplicates of 25 ul of lysate from each tube were transferred to micro-beta plates for assay using the Promega Dual Luciferase Reporter assay kit. Promoter activity was expressed as relative firefly luciferase activity normalized against Renilla luciferase activity. We determined the luciferase activity in cell lysates by luminescence spectroscopy. For each type of transfection, results were normalized to renilla luciferase counts.

To test for the effect of inflammation on FcγRIIB promoter activity, and to examine the basal and cytokine-induced promoter activity of the allelic variant constructs, we treated the U937 cells transfected with different allelic variants of the FcγRIIB promoter with gamma interferon (IFN-γ) and dexamethasone (DEX). Following IFN-γ treatment we detected upregulation in promoter activity of the C mutant (1.37+/−0.86), the A mutant (1.61+/−0.85) and the C+A double mutant(2.45+/−1.21) as compared to the wild type (−385G). IFN-γ downregulated the promoter activity (52–65.3%) compared to the baseline promoter activity. IFN-γ decreases the expression of the FcγRIIB in monocytes at RNA and protein level. Experiments using Dexamethasone (a therapeutic corticosteroid) were performed because the −385 G to C mutation is located within a glucocorticoid response element (GRE). There was an increase in promoter activity in the C+A double mutant (2.09+/−2.37) as compared to the wild type in Dex-treated cells, although these results are preliminary. Dex downregulated the promoter activity (53.6) as compared to the baseline promoter activity. The C mutant showed less downregulation 71.4% as compared to the WT (53.6) but this difference did not reach statistical significance.

The results suggest that the −385C and the −119A mutations did not significantly change the FcγRIIB baseline promoter activity, as assessed "in vitro" by measuring the luciferase activity in cell lysates of U937 cells, transfected with the respective mutated promoter constructs. The presence of both mutations (−385C)+(−119A) in the promoter construct resulted in a significant (p=0.0163) increase in promoter activity (2.16±1.031 fold, n=6), as compared to the WT construct.

EXAMPLE 3

Polymorphisms in the Promoter of FcγRIIB and Relative Expression and Function of FcγRIIB in Primary Monocytes and B Cells Studies were performed to determine whether there was a correlation between specific promoter alleles and levels of FcγRIIB expression in peripheral blood monocytes and B cells.

Real Time PCR

Total RNA was extracted from monocytes, purified by CD14 positive selection, using TRIzol reagent (Life Technologies) and reverse transcribed with the SuperScript Preamplification System (Life Technologies), all according to manufacturer instructions. For FcγRIIB transcript expression, real time RT-PCR assay was used. The SYBR Green PCR Core Reagents kit (PE Biosystems) was used with the iQ Multi-Color Real Time PCR Detection System (Bio-Rad) to amplify FcγRIIB1, and FcγRIIB2 in samples of cDNA derived from monocytes. The real time PCR reaction consisted of 45 cycles of 94° C. for 20 min. and 53° C. for 20 min. Primers pairs were designed specifically for FcγRIIB1 5'-GCAGGGAAATAAGAGAGACC-3' (SEQ ID NO: 16) and 5'-CTC AGC CAT AAC TTT GTC AGC-3' (80 bp amplicon)(SEQ ID NO: 17), FcγRIIB2 5'-GGGATGAT-TGTGGCTGTG-3' (SEQ ID NO: 18) and 5'-ATT AGT GGG ATT GGC TGAA-3' (106 bp amplicon) (SEQ ID NO: 19) as well as FcγRIIA 5'-GAC TAC GGA TAC CCA AAT GTC-3' (SEQ ID NO: 20) and 5'-AAGCCAGCAGCAG-CAAAA-3' (86 bp amplicon) (SEQ ID NO: 21) and GAPDH, as controls. During amplification, absorption readings were taken as a measure of the relative amount of amplicon produced in each cycle. These data were used to make a relative determination of FcγRIB expression.

Evaluation of FcγRIIB Protein Expression in B Cells by Flow-Cytometry.

Peripheral blood mononuclear cells were obtained from heparinized blood of normal controls and SLE patients after Ficoll-Hypaque density gradient centrifugation. B cells were identified by characteristic forward and side scatter and by anti-CD19-PE binding. Fluorescein-conjugated anti-pan-FcγRII mAb (FLI8.26-FITC) were obtained from Research Diagnostic Inc. (Pleasantville, N.J.). Evaluation of FcγRIIb expression on CD19 positive B cells was done by standard two-color flow-cytometry on a FACScan in the Flow Cytometry Core Facility.

Results

Analysis of the expression of FcγRIIB2 transcripts by Real time PCR in monocytes indicated a 2.57 fold increase in FcγRIIB2 RNA expression in a donor bearing the −385C/C−119T/A genotype as compared with the FcγRIIB2 RNA expression in control monocytes, isolated from a donor bearing the common genotype (−385G/G−119T/T). Analysis of FcγRIIB protein expression in the same donors by flow cytometry, by staining CD19-PE positive B cells with anti-FcγRII mAb (FLI8.26-FITC) indicated an increased mean fluorescence intensity (36.7%) in the −385C/C−119T/A donor vs the −385G/G−119T/T (127.1 vs 93.0). The increase (57.5%) persisted in the −385C/C−119T/A B cells after the cells were cultured overnight in medium (66.43 vs 42.18). An increase (49.0%) in FcγRIIB expression was also detected in the −385C/C−119T/A B cells following overnight culture in medium supplemented with IL-4 (100 ng/ml).

The results suggest that the −385C and −119A allelic polymorphism in the FcγRIIB promoter may result in upregulation of FcγRIIB expression at RNA and protein level, as observed by analyzing the differential promoter activity "in vitro" in the reporter gene assay.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties. Citation of any reference in this application should not be construed as an admission that the reference is prior art to the invention.

REFERENCES

1. Salmon, J. E., and L. Pricop. Human receptors for immunoglobulin G: key elements in the pathogenesis of rheumatic disease. Arthritis Rheum 2001; 44:739–750.
2. Tsao, B. P., R. M. Cantor, K. C. Kalunian, C. J. Chen, H. Badsha, R. Singh, D. J. Wallace, R. C. Kitridou, S. L. Chen, N. Shen, Y. W. Song, D. A. Isenberg, C. L. Yu, B. H. Hahn, and J. I. Rotter. Evidence for linkage of a candidate chromosome 1 region to human systemic lupus erythematosus. J Clin Invest 1997; 99:725–731.
3. Gaffney, P. M., G. M. Kearns, K. B. Shark, W. A. Ortmann, S. A. Selby, M. L. Malmgren, K. E. Rohlf, T. C. Ockenden, R. P. Messner, R. A. King, S. S. Rich, and T. W. Behrens. A genome-wide search for susceptibility genes in human systemic lupus erythematosus sib-pair families. Proc Natl Acad Sci U S A 1998; 95:14875–14879.
4. Moser, K. L., B. R. Neas, J. E. Salmon, H. Yu, C. Gray-McGuire, N. Asundi, G. R. Bruner, J. Fox, J. Kelly, S. Henshall, D. Bacino, M. Dietz, R. Hogue, G. Koelsch, L. Nightingale, T. Shaver, N. I. Abdou, D. A. Albert, C. Carson, M. Petri, E. L. Treadwell, J. A. James, and J. B. Harley. Genome scan of human systemic lupus erythematosus: Evidence for linkage on chromosome 1q in African-American pedigrees. Proc Natl Acad Sci U S A 1998; 95:14869–14874.
5. Shai, R., F. P. Quismorio, Jr., L. Li, O. J. Kwon, J. Morrison, D. J. Wallace, C. M. Neuwelt, C. Brautbar, W. J. Gauderman, and C. O. Jacob. Genome-wide screen for systemic lupus erythematosus susceptibility genes in multiplex families. Hum Mol Genet 1999; 8:639–644.
6. Gray-McGuire, C., K. L. Moser, P. M. Gaffney, J. Kelly, H. Yu, J. M. Olson, C. M. Jedrey, K. B. Jacobs, R. P. Kimberly, B. R. Neas, S. S. Rich, T. W. Behrens, and J. B. Harley. Genome scan of human systemic lupus erythematosus by regression modeling: evidence of linkage and epistasis at 4p16–15.2. Am J Hum Genet 2000; 67:1460–1469.
7. Salmon, J. E., S. Millard, L. A. Schachter, F. C. Arnett, E. M. Ginzler, M. F. Gourley, R. Ramsey-Goldman, M. G. Peterson, and R. P. Kimberly. Fc gamma RIIA alleles are heritable risk factors for lupus nephritis in African Americans. J Clin Invest 1996; 97:1348–1354.
8. Wu, J., J. C. Edberg, P. B. Redecha, V. Bansal, P. M. Guyre, K. Coleman, J. E. Salmon, and R. P. Kimberly. A novel polymorphism of FcgammaRIIIa (CD16) alters receptor function and predisposes to autoimmune disease. J Clin Invest 1997; 100:1059–1070.
9. Manger, K., R. Repp, B. M. Spriewald, A. Rascu, A. Geiger, R. Wassmuth, N. A. Westerdaal, B. Wentz, B. Manger, J. R. Kalden, and J. G. van de Winkel. Fcgamma receptor IIa polymorphism in Caucasian patients with systemic lupus erythematosus: association with clinical symptoms. Arthritis Rheum 1998; 41:1181–1189.
10. Salmon, J. E., S. Ng, D. H. Yoo, T. H. Kim, S. Y. Kim, and G. G. Song. Altered distribution of Fcgamma receptor IIIA alleles in a cohort of Korean patients with lupus nephritis. Arthritis Rheum 1999; 42:818–819.
11. Koene, H. R., M. Kleijer, A. J. Swaak, K. E. Sullivan, M. Bijl, M. A. Petri, C. G. Kallenberg, D. Roos, A. E. von dem Borne, and M. de Haas. The Fc gammaRIIIA-158F allele is a risk factor for systemic lupus erythematosus. Arthritis Rheum 1998; 41:1813–1818.
12. Zuniga, R., S. Ng, M. G. Peterson, J. D. Reveille, B. A. Baethge, G. S. Alarcon, and J. E. Salmon. Low-binding alleles of Fcgamma receptor types IIA and IIIA are inherited independently and are associated with systemic lupus erythematosus in Hispanic patients. Arthritis Rheum 2001; 44:361–367.
13. Seligman, V. A., C. Suarez, R. Lum, S. E. Inda, D. Lin, H. Li, J. L. Olson, M. F. Seldin, and L. A. Criswell. The Fcgamma receptor IIIA-158F allele is a major risk factor for the development of lupus nephritis among Caucasians but not non-Caucasians. Arthritis Rheum 2001; 44:618–625.
14. Botto, M., E. Theodoridis, E. M. Thompson, H. L. Beynon, D. Briggs, D. A. Isenberg, M. J. Walport, and K. A. Davies. Fc gamma RIIa polymorphism in systemic lupus erythematosus (SLE): no association with disease. Clin Exp Immunol 1996; 104:264–268.
15. Smyth, L. J., N. Snowden, D. Carthy, C. Papasteriades, A. Hajeer, and W. E. Ollier. Fc gamma RIIa polymorphism in systemic lupus erythematosus. Ann Rheum Dis 1997; 56:744–746.
16. Oh, M., M. A. Petri, N. A. Kim, and K. E. Sullivan. Frequency of the Fc gamma RIIIA-158F allele in African American patients with systemic lupus erythematosus. J Rheumatol 1999; 26:1486–1489.
17. Lehrnbecher, T., C. B. Foster, S. Zhu, S. F. Leitman, L. R. Goldin, K. Huppi, and S. J. Chanock. Variant genotypes of the low-affinity Fcgamma receptors in two control populations and a review of low-affinity Fcgamma receptor polymorphisms in control and disease populations. Blood 1999; 94:4220–4232.
18. Gaffney, P. M., K. L. Moser, R. R. Graham, and T. W. Behrens. Recent advances in the genetics of systemic lupus erythematosus. Rheum Dis Clin North Am 2002; 28:111–126.
19. Bolland, S., and J. V. Ravetch. Inhibitory pathways triggered by ITIM-containing receptors. Adv Immunol 1999; 72:149–177.
20. Malbec, O., W. H. Fridman, and M. Daeron. Negative regulation of hematopoietic cell activation and proliferation by Fc gamma RIIB. Curr Top Microbiol Immunol 1999; 244:13–27.
21. Takai, T., M. Ono, M. Hikida, H. Ohmori, and J. V. Ravetch. Augmented humoral and anaphylactic responses in Fc gamma RII-deficient mice. Nature 1996; 379:346–349.
22. Clynes, R., J. S. Maizes, R. Guinamard, M. Ono, T. Takai, and J. V. Ravetch. Modulation of Immune Complex-induced Inflammation In Vivo by the Coordinate Expression of Activation and Inhibitory Fc Receptors. J Exp Med 1999; 189:179–186.
23. Yuasa, T., S. Kubo, T. Yoshino, A. Ujike, K. Matsumura, M. Ono, J. V. Ravetch, and T. Takai. Deletion of Fcgamma Receptor IIB Renders H-2(b) Mice Susceptible to Collagen-induced Arthritis. J Exp Med 1999; 189:187–194.
24. Bolland, S., and J. V. Ravetch. Spontaneous autoimmune disease in Fc(gamma)RIIB-deficient mice results from strain-specific epistasis. Immunity 2000; 13:277–285.
25. Luan, J. J., R. C. Monteiro, C. Sautes, G. Fluteau, L. Eloy, W. H. Fridman, J. F. Bach, and H. J. Garchon. Defective Fc gamma RII gene expression in macrophages of NOD mice: genetic linkage with up-regulation of IgG1 and IgG2b in serum. J Immunol 1996; 157:4707–4716.
26. Pritchard, N. R., A. J. Cutler, S. Uribe, S. J. Chadban, B. J. Morley, and K. G. Smith. Autoimmune-prone mice share a promoter haplotype associated with reduced expression and function of the Fc receptor FcgammaRII. Curr Biol 2000; 10:227–230.
27. Jiang, Y., S. Hirose, M. Abe, R. Sanokawa-Akakura, M. Ohtsuji, X. Mi, N. Li, Y. Xiu, D. Zhang, J. Shirai, Y. Hamano, H. Fujii, and T. Shirai. Polymorphisms in IgG Fc receptor IIB regulatory regions associated with autoimmune susceptibility. Immunogenetics 2000; 51:429–435.
28. C. Kyogoku, H. M. Dijstelbloem, N. Tsuchiya, Y. Hatta, H. Kato, A. Yamaguchi, T. Fukazawa, M. D. Jensen, H. Hashimoto, J. G. J. van de Winkel, C. G. M. Kallenberg and K. Tokunaga, poster entitled "Association of Fcg receptor gene polymorphisms in Japanese patients with systemic lupus erythematosus", presented at The Lupus Genetics Conference in Oklahoma City, on Sept. 9, 2001.
29. K. Su, J. C. Edberg, J. Wu, S. E. McKenzie, R. P. Kimberly, poster entitled "Single nucleotide polymorphisms in the FcgRIIB gene promoter which alter receptor expression and associate with systemic lupus erythematosus in African-Americans" presented at the Annual Scientific Meeting of the American College of Rheumatology, held in San Francisco, on Nov. 10–15, 2001.

What is claimed is:

1. A method for assessing whether an individual has or is susceptible to development of systemic lupus erythematosus comprising comparing
   (a) a test polymorphic pattern comprising at least one polymorphic position within an FcγRIIB promoter gene of the individual, with
   (b) a reference polymorphic pattern derived from a population of individuals having systemic lupus erythematosus. wherein the reference polymorphic pattern comprises a C residue at position −385 and/or an A residue at position −119; and
   (c) concluding whether the individual is susceptible to development of systemic lupus erythematosus wherein identity between at least one polymorphism included in the test polymorphic pattern and at least one polymorphism included in the reference polymorphic pattern indicates that the individual has or is susceptible to development of systemic lupus erythematosus.

2. The method of claim 1, wherein the reference polymorphic pattern comprises at least one polymorphism.

3. The method of claim 2 wherein the polymorphic pattern comprises −385 C/C.

4. The method of claim 2 wherein the polymorphic pattern comprises −119 T/A.

5. The method of claim 2 wherein the polymorphic pattern comprises −119 A/A.

6. The method of claim 1, wherein the reference polymorphic pattern comprises at least two polymorphisms.

7. The method of claim 6 wherein the polymorphic pattern comprises −385 C/C and −119 T/A.

* * * * *